United States Patent [19]

Quadri

[11] Patent Number: 5,133,725
[45] Date of Patent: * Jul. 28, 1992

[54] ADJUSTABLE INTRA-LIMINAL VALVULOTOME

[75] Inventor: Arshad Quadri, Pittsfield, Mass.

[73] Assignee: Berkshire Research and Development, Inc., Pittsfield, Mass.

[*] Notice: The portion of the term of this patent subsequent to Sep. 17, 2008 has been disclaimed.

[21] Appl. No.: 614,114

[22] Filed: Nov. 16, 1990

Related U.S. Application Data

[63] Continuation-in-part of Ser. No. 390,410, Aug. 7, 1989, Pat. No. 5,049,154.

[51] Int. Cl.⁵ .............................................. A61B 17/32
[52] U.S. Cl. .................................... 606/159; 606/171
[58] Field of Search ............... 606/159, 170, 171, 160; 128/751, 752; 604/22

[56] References Cited

U.S. PATENT DOCUMENTS

| | | | |
|---|---|---|---|
| 518,600 | 4/1894 | Hallman | 606/170 |
| 2,655,154 | 10/1953 | Richter | 606/159 |
| 3,404,677 | 10/1968 | Springer | 128/751 |
| 4,200,111 | 4/1980 | Harris | 128/751 |
| 4,655,217 | 4/1987 | Reed | 606/159 |
| 4,768,508 | 9/1988 | Chin et al. | 606/159 |
| 5,049,154 | 9/1991 | Quadri | 606/159 |

FOREIGN PATENT DOCUMENTS 1266446 4/1968 Fed. Rep. of Germany ...... 606/170

Primary Examiner—Michael H. Thaler
Attorney, Agent, or Firm—Mason, Fenwick & Lawrence

[57] ABSTRACT

An adjustable intraluminal valvulotome comprises a hollow tubular member and a pair of substantially identical, opposed cutting blades provided at the distal end of the tubular member. Each of the cutting blades has a first cutting blade at its trailing edge and a second cutting blade at one side generally transverse to the first cutting blade. The outer faces of the cutting blades have a complex convex surface. The cutting blades are movable between an extended position and a retracted position with respect to the distal end of the tubular member and between an open position in which the cutting blades are spaced apart from each other and a closed position in which said cutting blades are drawn tightly against each other, by the operation of a pair of spring wires respectively attached to the cutting blades and slidable within the tubular member. The distal end of the tubular member is provided with a receptacle for receiving the first cutting edges of the cutting blades in the retracted position. A coil spring can be provided within the tubular member, through which the spring wires pass, to facilitate movement of the cutting blades between their open and closed positions.

8 Claims, 5 Drawing Sheets

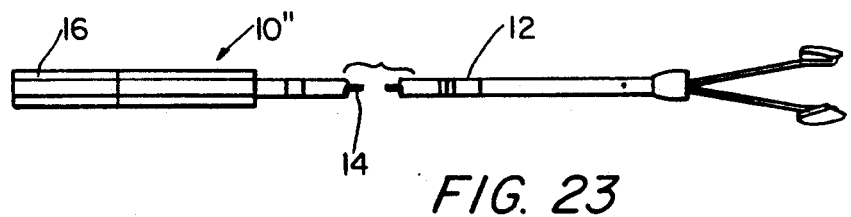
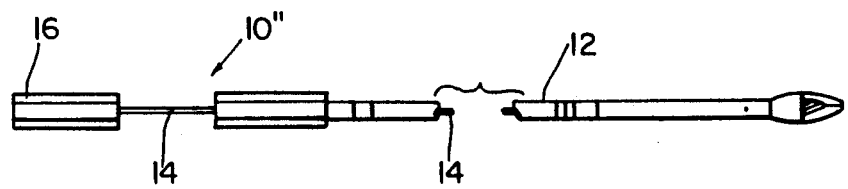
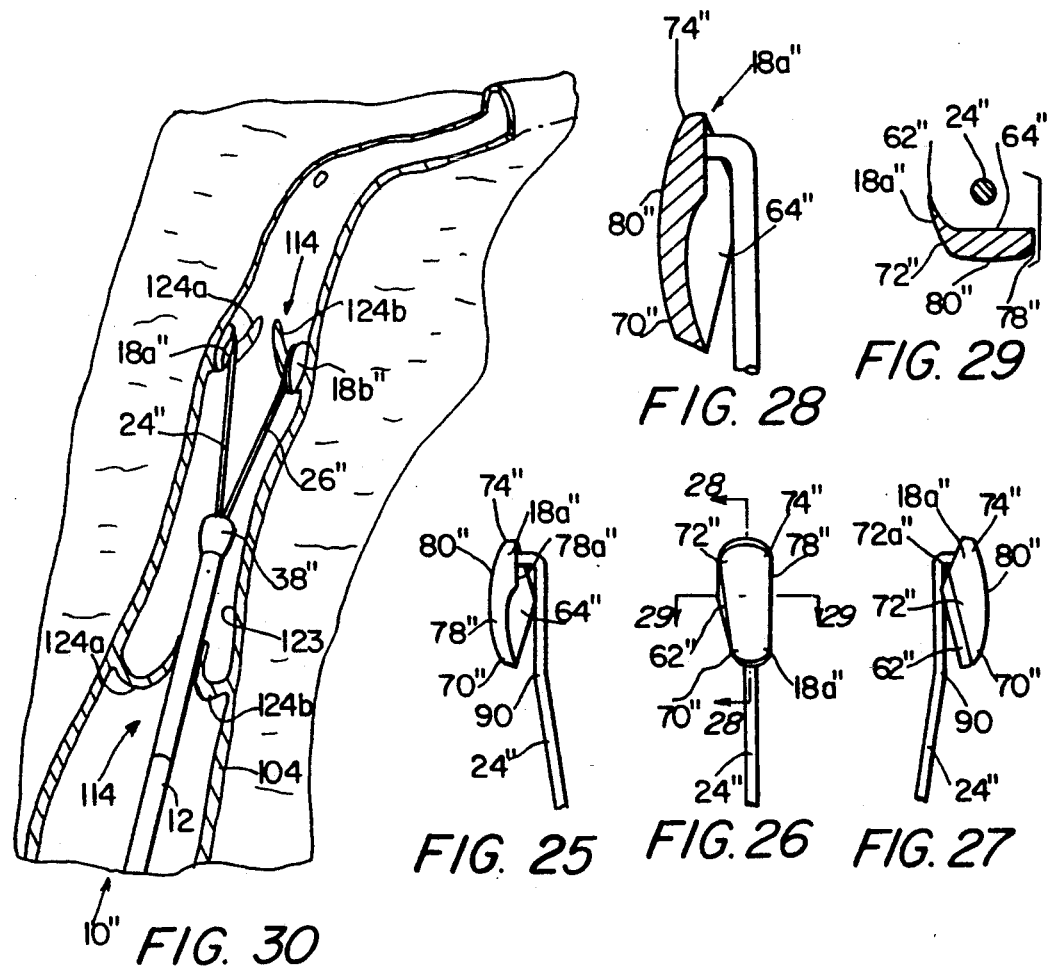

ADJUSTABLE INTRA-LIMINAL VALVULOTOME

This application is a continuation-in-part of my U.S. application Ser. No. 390,410 filed Aug. 7, 1989, now U.S. Pat. No. 5,049,154.

FIELD OF THE INVENTION

This invention relates to an intra-luminal valvulotome for vascular surgery and more particularly, to such a valvulotome whose blades can be remotely retracted, extended, and adjusted to a method of using such a valvulotome.

BACKGROUND OF THE INVENTION

Many individuals, particularly the elderly, suffer from deposits which clog their arteries, more commonly referred to as atherosclerosis. Quite frequently, these deposits block or restrict the flow of blood in the arteries of the lower extremities, which limits the flow of blood to the patient's leg and foot. Lack of blood flow and oxygen to the leg and foot may be debilitating or life-threatening to the individual, and corrective measures must be taken.

Although some individuals may be treated with medication, in most cases surgery is required. Some arterial deposits may be removed or the arteries dilated with various surgical techniques, but these procedures do not work for every patient for very long. The condition may recur, requiring further action.

One procedure which has proven effective in combating atherosclerosis is to bypass the blocked artery with another blood carrying conduit. Experimentation has lead many surgeons to use synthetic type materials for replacement arteries. Such materials include an artificial tube made from Dacron or plastic. Although temporarily suitable, these artificial conduits have a tendency to become clogged once again, and therefore their use has been restricted especially in distal bypasses.

The preferred material for an arterial bypass is one of the individual's own veins. More particularly, when the femoral artery in the leg becomes blocked, it is desirable to use the greater long saphenous vein to bypass the blocked artery.

There are two ways in which a surgeon may use the individual's own vein. The vein may be harvested from the patient's leg, removed from the patient's body, and turned end for end before resetting the vein back into the body to be used to bypass the blocked artery. Turning the vein end for end ensures that the valves are oriented in the proper direction to allow the flow of blood from the heart to the leg and foot. Although this procedure is commonly used, it interferes with the integrity of the vein and long segments of small diameter veins may become blocked in the short or long term.

A second and preferred procedure is an in-situ saphenous vein bypass. During this procedure, the vein is left in place in the patient's leg, while portions of the vein are connected to the femoral artery in such a manner as to bypass the blocked portion of the artery. If the procedure were to stop here, however, the valves in the vein would prevent the flow of blood down to the leg. Therefore, an instrument called a valvulotome has been developed which is inserted into the vein to lyse or rupture and render incompetent the valves in the bypass vein.

There are two or three valvulotome instruments available today. Each is quite similar in that it includes a small cutting blade mounted on a thin stainless steel wire. To use the instrument, the surgeon makes an incision and inserts the blade into the patient's vein. The instrument is advanced into the vein past the valve which is the farthest from the incision. When the blade of the valvulotome has been pushed past the farthest valve, the surgeon then begins pulling back on the wire forcing the blade to engage with the valve cusps thereby perforating the valve and rendering it inoperative.

The blades currently in use are of several shapes. One shape is a "J" or "hook-shaped" blade which has a cutting edge on the inside of the curved portion of the hook. Another popular shape is an inverted "U" or "mushroom-shaped" blade. Other shapes are also available but all are restricted in that they have only one cutting edge. Several serious complications have arisen however with the use of these types of blades. Most problematic has been that although the blade is designed to engage with and perforate the valve cusps, it also frequently engages with and perforates the walls of the vein as the blade is pulled back through the vein. Since the vein has a tremendous number of branches, there is also the danger that the blade may snag and engage with the opening leading to these branches, and lyse this junction. When this occurs, remedial surgery must be performed to correct the inadvertent and unwanted rupture.

A further problem arises in that the existing blades do not always satisfactorily lyse the valves to allow for a sufficient amount of blood to the leg and foot. Valve cusps are shaped and are attached to the vein's "cup" hingeably inner wall. When the cusps close, they contact one another and the backward flow of blood pushes these cusps securely against one another, preventing any further backward flow. Since current valvulotome blades have only one cutting edge, the value cusps may not be sufficiently disabled, or only one cusp may be disabled at one time in the case of the "J" blade.

An additional problem with the current blade designs is that the blade is of one size while the vein itself is tapered having a larger diameter near the groin area and becomes narrower near the ankle. This causes further complications in trying to perforate valve cusps without causing trauma to the inner wall of the vein. In addition, since the blade is not retractable, it cannot be pulled back once inserted into the vein without engaging with the valves or other portions of the vein.

SUMMARY OF INVENTION

It is therefore an object of this invention to provide an improved valvulotome in which the blade can be extended for cutting and retracted to a shielded position.

It is a further object of this invention to provide such a valvulotome in which extension and retraction of the blade can be controlled from a remote location outside of the body.

It is a still further object of this invention to provide such a valvulotome which minimizes trauma to the inner wall of a vein.

It is a still further object of this invention to provide such a valvulotome having more than one blade, each blade having multiple cutting edges perpendicular to each other to ensure complete perforation of the valve cusps.

It is a further object of this invention to provide such a valvulotome in which the distance between the blades can be remotely adjusted to conform to the size of the vein.

It is a still further object of this invention to provide such a valvulotome which can be retrieved once inside the vein without causing an damage to the valves.

It is a further object of this invention to provide such a valvulotome which is inexpensive to manufacture and is disposable.

It is a still further object of this invention to provide such a valvulotome which has an end member capable of shielding the cutting edge of the blades allowing the instrument to be manipulated in the vein without trauma to the vein wall or vein branches.

It is a still further object of this invention to provide such a valvulotome which has an end member capable of shielding the cutting edge of the blades allowing the instrument to be manipulated in the vein without entering the vein branches.

This invention results from the realization that a truly novel and effective valvulotome can be achieved by using a plurality of cutting blades with two substantially transverse cutting edges whose separation may be varied remotely and which can be retracted into a shielded non-cutting position or extended into a cutting position, all remotely.

This invention features an adjustable intraluminal valvulotome including a hollow tubular member in which is slidably disposed a wire control member. First and second cutting blades are connected to one end of said wire control member by respective first and second wire connecting members. Means are provided proximate the other end of the wire control member for controlling longitudinal movement of the wire control member in and out of the tubular member. The means for controlling longitudinal movement of the wire member enables the first and second blades to move between a first extended cutting position and a second retracted position. Shielding means restrain the first and second cutting blades in the fully retracted, non-cutting position.

In a preferred embodiment, each of the first and second cutting blades includes first and second cutting edges which are substantially transverse to each other. The means for interconnecting the first and second cutting blades to the wire control member includes first and second wire elements each element having a first end attached to the first and second cutting blades respectively, and means for joining the second end of the first and second wire elements to the wire member. Means for joining the first and second wire elements to the wire member may include a welded joint. In one aspect of the invention, the wire elements comprise generally flat spring wire.

The valvulotome can further include means for generally indicating the distance of projection of the first and second cutting blades from the end of said tubular member. Means for indicating the interblade spacing between the first and second cutting blades when in the extended position can also be included. The means for shielding can include receptacle means for enclosing at least a portion of the first and second cutting blades.

This invention also features a method of using a valvulotome to rupture and render inoperative valves located in a vein, including making an incision in a vein whose valve is to be rendered inoperative and introducing into the vein an intraluminal valvulotome having a plurality of cutting blades. The method also includes advancing the cutting blades into the vein until the cutting blades are adjacent but not beyond the valve which is to be rendered inoperative. The method further includes extending the cutting blades into a cutting position beyond the valve, and at least partially retracting the cutting blades causing the blades to engage with the valve and thereby rupture and render inoperative the valve cusps. The cutting blades are then fully retracted into a shielded non-cutting position. If additional valves are to be rendered inoperative, the valvulotome is re-positioned within the vein until the cutting blades are adjacent but not beyond a subsequent valve that is to be rendered inoperative. The steps of extending the cutting blades, engaging the blades with the valve to rupture and render inoperative the valve, and fully retracting the cutting blades to a shielded non-cutting position are repeated as required, until all the valves in the vein that are desired to be rendered inoperative have been ruptured.

In one aspect of the invention, the method further includes inserting into the vein an angioscope and observing when the cutting blades have been extended past the valve to be rendered inoperative. In another aspect of the invention, the method can further include observing the ruptured valve with the angioscope to ensure that the valve has been rendered inoperative.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 23 is a side elevational view of a third embodiment of the adjustable intraluminal valvulotome according to the invention showing two cutting blades in the partially extended position;

FIG. 24 is a side elevational view of the valvulotome of FIG. 23 showing the two cutting blades in the retracted position;

FIG. 25 is a left side elevational view of a cutting blade of the valvulotome of FIG. 23;

FIG. 26 is a front elevational view of the cutting blade of FIG. 25;

FIG. 27 is a right side elevational view of the cutting blade of FIG. 25;

FIG. 28 is a cross-sectional view of the cutting blade of FIG. 25, taken along line 28—28 of FIG. 26;

FIG. 29 is a cross-sectional view of the cutting blade of FIG. 25, taken along line 29—29 of FIG. 26; and FIG. 30 is a lateral cross-sectional view of a vein with venous valve in which has been inserted the valvulotome of FIG. 23, showing the engagement of the blade cutting edges with the valve cusps.

DESCRIPTION OF THE PREFERRED EMBODIMENTS

Figure 1:
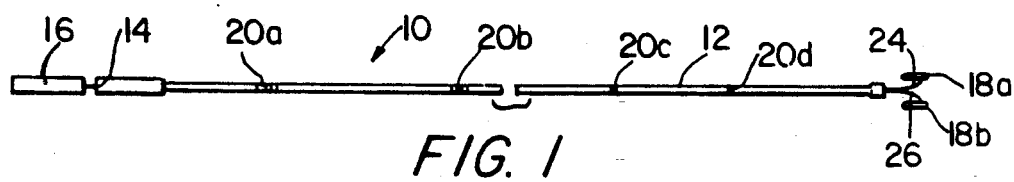
FIG. 1 is a side elevational view of a first embodiment of the adjustable intraluminal valvulotome according to this invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

An adjustable intraluminal valvulotome according to this invention, may be accomplished by providing a hollow tubular member in which is slidably disposed a wire member. Such a wire containing hollow tubular member may be fashioned from a standard endoscopic instrument utilized for performing biopsies. An example of such an instrument is available from American Edwards and is designated as having an outside diameter of 4 F. The instruments vary in length from 80 to 100 cm. Proximate one end of the wire, is a handle of plastic or other suitable material which facilitates sliding the wire through the tube. The wire member near the plastic handle may include graduation marks to generally indicate the longitudinal distance the wire is extended outwardly from the end of the tubular member, as well as the inter-blade spacing between the two cutting blades. Typically, the blades may be extended from two to three centimeters in distance outward from the end of the tubular member, at which Point the interblade spacing may be as wide as approximately 2 mm to 5 mm.

Each cutting blade is mounted on a flat spring-loaded wire element. The spring action of the wire serves to increase the interblade or radial spacing as the blades are extended longitudinally outward from the tubular member. Each wire element is joined at a common point to the wire member by means such as soldering or welding.

As the blades are retracted, a small-diameter hole or aperture in the end of the tubular member through which the wire elements pass, causes the blades to pull in closely together. As the user begins retracting the blades, the blades engage with and cut the valve cusps to render inoperative a valve within a vein. After the valve cusps have been ruptured, the blades are in a partially retracted intermediate position. The blades may be further, fully retracted into a shielded, non-cutting position. The blades may rest against a bullet or nozzle shaped end member which serves to shield the cutting edges of the blades from contact with any external surface. In a preferred embodiment, the end of the tubular member may include a receptacle which serves to surround and contain at least a portion of the two cutting blades to shield them from contact with the vein.

Each cutting blade may be made of stainless steel and electronically welded to its associated flat spring wire. The blades are approximately 3 to 4 mm in length, 2 mm in width, and 1 mm in thickness. The flat spring wire should be of appropriate size for individual attachment to the blades at one end, and attachment together to the wire member at the other end. Any edge or corner of the cutting blades which is not to be used for cutting is rounded or polished to avoid damaging the inner wall of the vein.

Figure 2:
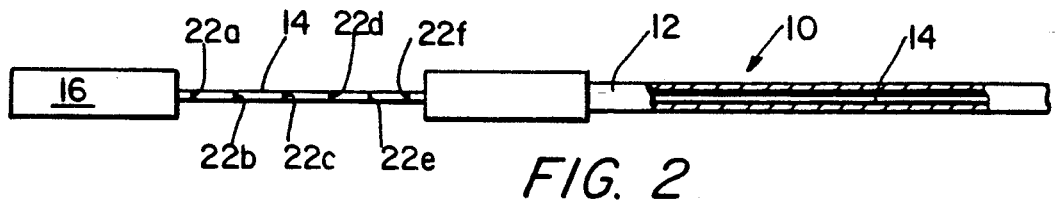
FIG. 2 is a detailed side elevational view partially cut away of the means for controlling the movement of the control wire and cutting blades through the hollow tubular member of the valvulotome of FIG. 1 and further showing graduation marks for gauging the extended position of the cutting blades.
Figure 3:
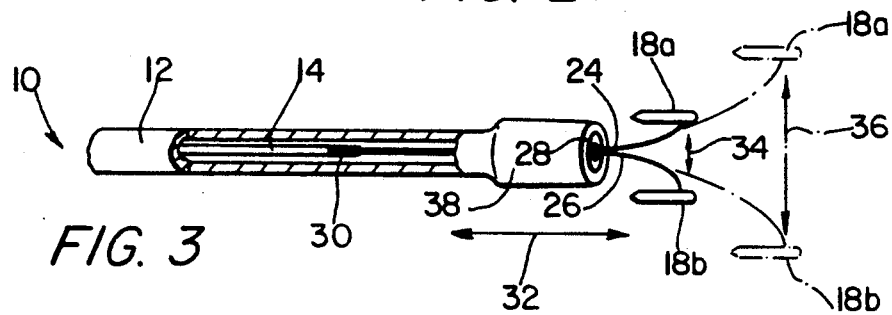
FIG. 3 is a detailed side elevational view of the end member of the valvulotome of FIG. 1 showing two cutting blades in the partially extended position.

Referring now to FIGS. 1-3, in a first embodiment, the adjustable intraluminal valvulotome 10 includes a hollow tubular member 12 through which is slidably mounted a wire member 14. Attached to one end of wire 14 is a handle 16. Cutting blades 18a and 18b are mounted to the other end of the wire member. Hollow tubular member 12 includes markings 20a-20d which serve to indicate how far into the vein the valvulotome has been advanced.

As shown in FIG. 2, wire member 14 also includes graduation markings 22a-22f which serve as a guide to indicate the interblade spacing between the two cutting blades.

Referring now to FIG. 3, cutting blades 18a and 18b are mounted to spring wire elements 24 and 26, respectively. Wire elements 24 and 26 pass through narrow aperture 28 in an end member 38. As will be described in greater detail hereinafter, end member 38 serves to restrain cutting blades 18a, 18b and hold them in the non-cutting position when fully retracted.

Wire elements 24 and 26 are attached to wire member 14 at joint 30, as shown in FIG. 3, e.g. by welding. Wire element 14 is slidably movable in hollow member 12 in the direction of arrow 32. Slidably moving wire member 14 causes cutting blades 18a and 18b to extend from the fully retracted position shown in FIG. 4 to the intermediate position shown in FIG. 3, in which cutting blades 18a and 18b move apart from each other, shown by interblade spacing arrow 34, and then to a fully extended position indicated by the dashed lines, achieving the interblade spacing indicated by dashed arrow 36.

Figure 4:
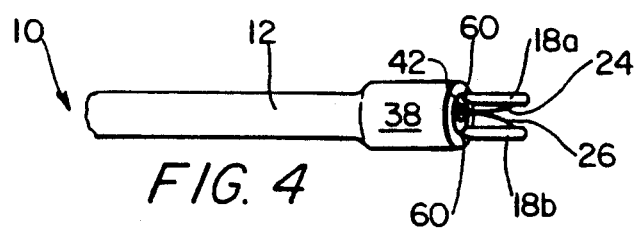
FIG. 4 is a side elevational view of an end member of the valvulotome of FIG. 1 showing the blades in the retracted position.
Figure 11:
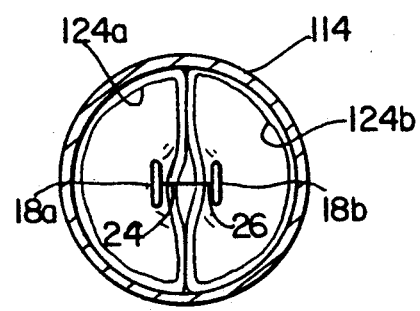
FIG. 11 is a cross sectional view of the vein and venous valve of FIG. 10 showing the engagement of the blade cutting edges with the valve cusps.

Referring now to FIGS. 3 and 4, hollow tubular member 12 includes end member 38 which serves as a receptacle to shield cutting blades 18a and 18b from contact with the surrounding tissue when in the fully retracted position. End member 38 includes a cavity 42 in which rest first cutting edges 60 of blades 18a and 18b, as shown in FIG. 4. Side cutting edges 62 of cutting blades 18a and 18b are shielded by virtue of the fact that in the retracted position, they are back to back facing one another, as shown in FIG. 11, and cannot come in contact with the vein or other object.

Figure 5:
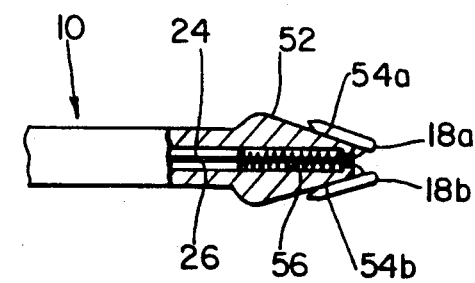
FIG. 5 is an alternative embodiment of the receptacle end of the valvulotome of FIG. 1 with the blade in the retracted position and the cutting edges secured against the receptacle.

Alternatively, as shown in FIG. 5, end member 52 can be in the form of a tear drop or other tapered shape which allows cutting blades 18a and 18b to rest against side wall areas 54a and 54b of end member 52 in the tapered area which is substantially smaller than the maximum diameter of end member 52 and on its trailing end, for shielding cutting blades 18a and 18b in the fully retracted position. Additionally, narrow aperture 28 can be defined by a coiled spring 56. Wire elements 24 and 26 pass through the center of the spring 56. As blades 18a and 18b are extended, wire elements 24 and 26 push against and expand the portion of the spring 56 forming aperture 28. As blades 18a and 18b are retracted, spring 56 forces aperture 28 to narrow, thus keeping cutting blades 18a and 18b tightly against end member 52. A spring 56 similarly can be used in end member 38.

Figure 6:
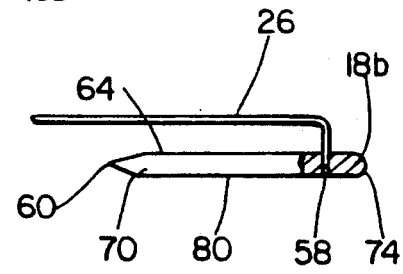
FIG. 6 is a side elevational view partially cut away of a cutting blade of the valvulotome of FIG. 1.

As shown in FIG. 6, cutting blade 18b is attached to flat spring wire element 26. Spring wire element 26 can be inserted through a hole 58 in the inner face 64 of cutting blade 18b and welded into position. An identical arrangement is used to attach spring wire element 24 to cutting blade 18a.

Figure 7:
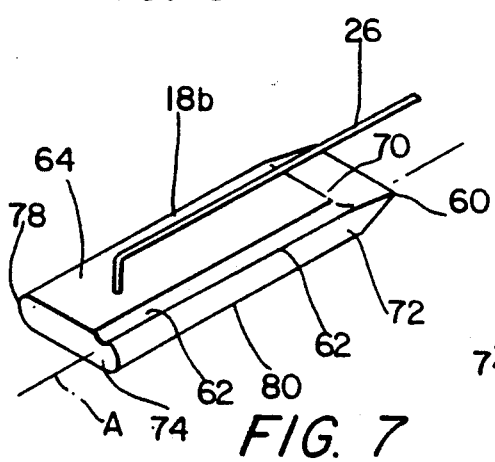
FIG. 7 is a perspective view of a first embodiment of the cutting blade for the valvulotome of FIG. 1 showing a base cutting edge and a vertical cutting edge formed by grinding a channel in the blade.
Figure 8:
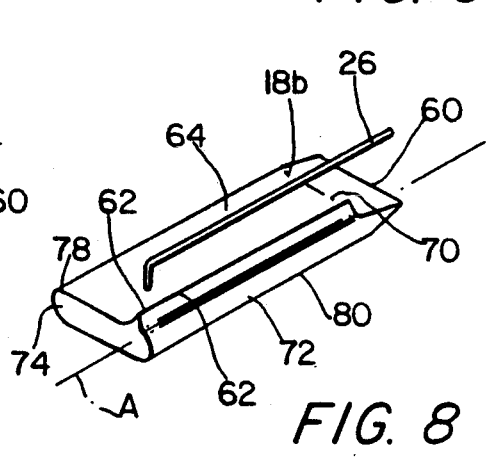
FIG. 8 is a perspective view of a second embodiment of the cutting blade for the valvulotome of FIG. 1 showing a vertical cutting edge formed by a protrusion on a planar surface of the blade.

First and second embodiments of the cutting blade of the valvulotome of FIG. 1 are shown in FIGS. 7 and 8, respectively. FIGS. 7 and 8 illustrate a cutting blade 18b, it being understood that the description herein of cutting blade 18b is equally applicable to cutting blade 18a.

Referring now to FIG. 7, the first embodiment of blade 18b includes first or rearward cutting edge 60 along the trailing edge 70 of the blade, as well as second or side cutting edge 62 along one side 72 of the blade transverse to cutting edge 60 and generally parallel to longitudinal axis A of cutting blade 18b. In the first embodiment, side cutting edge 62 can be fashioned by grinding a depression 162 on blade 18b inwardly of side 72. Alternatively, in the second embodiment, side cutting edge 62 can be fashioned by providing a raised cutting edge 262 inwardly of side 72, also aligned with longitudinal axis A of cutting blade 18b. All remaining edges such as leading edge 74 and side edge 78 of cutting blade 18b are well-rounded to avoid sharp edges which might damage the inner wall of a vein.

Figure 14:
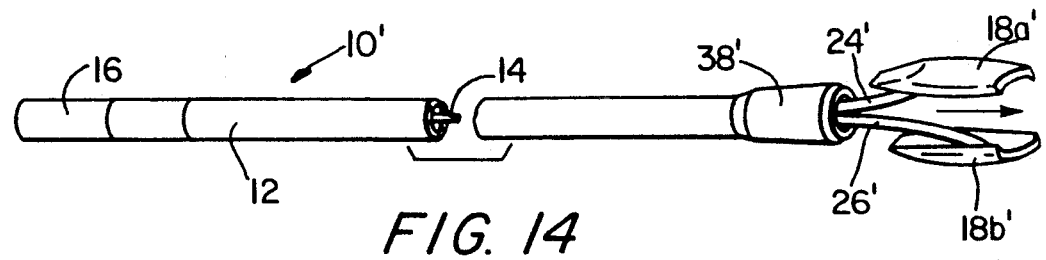
FIG. 14 is a side perspective view of a second embodiment of the adjustable intraluminal valvulotome according to the invention showing two cutting blades in the partially extended position.
Figure 15:
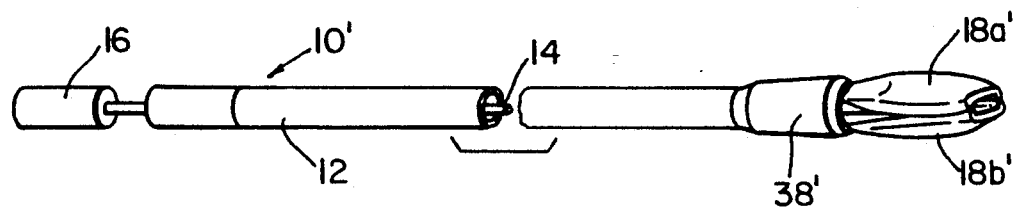
FIG. 15 is a side perspective view of the valvulotome of FIG. 14 showing the two cutting blades in the retracted position.

Referring now to FIGS. 14-22, there is shown a second embodiment of the adjustable intraluminal valvulotome 10' according to the invention. As shown in FIGS. 14 and 15, valvulotome 10' includes a hollow tubular member 12, a wire member 14, and a handle 16 essentially identical to hollow tubular member 12, wire member 14, and handle 16, respectively, described above with respect to valvulotome 10 shown in FIGS. 1-8. Cutting blades 18a' and 18b' are mounted to spring wire elements 24' and 26', respectively, and spring wire elements 24' and 26' are attached to wire member 14 at a joint 30 as shown in FIG. 3 with respect to valvulotome 10. Valvulotome 10' differs from valvulotome 10 in the configuration of its cutting blades 18a' and 18b'.

Figure 16A:
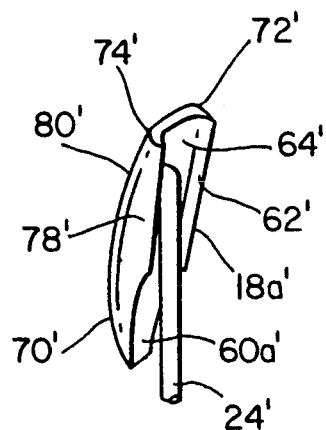
FIGS. 16a and 16b are right and left side perspective views, respectively, of a cutting blade of the valvulotome of FIG. 14.
Figure 16B:
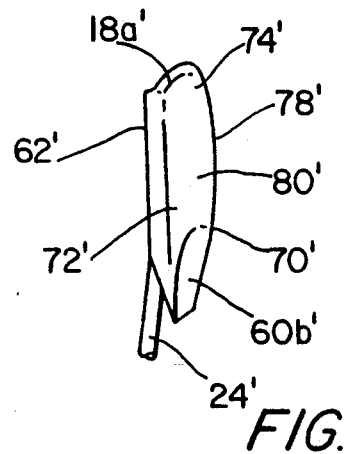
Figure 17A:
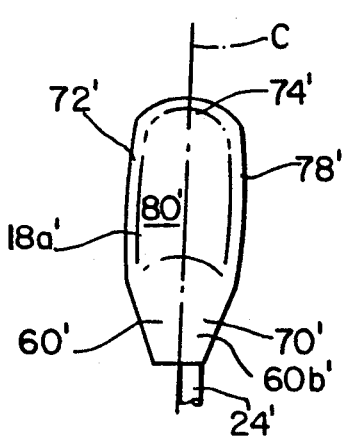
FIGS. 17a and 17b are front and back perspective views, respectively, of a cutting blade of the valvulotome of FIG. 14.
Figure 17B:
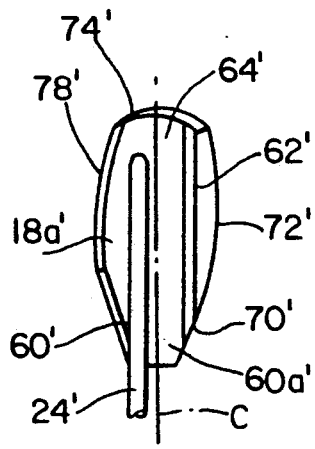
Figure 18:
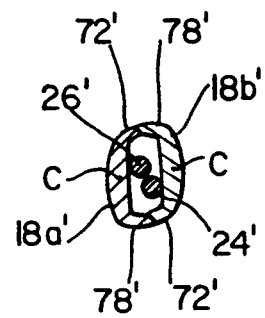
FIG. 18 is a cross-sectional view of the cutting blades of the valvulotome of FIG. 14 in the retracted position.

As can be seen from FIGS. 16-18, cutting blades 18a' and 18b' are identical. Referring to FIGS. 16 and 17, cutting blade 18a' is shown, it being understood that as cutting blades 18a' and 18b' are identical, they will both be described with respect to FIGS. 16 and 17.

Like cutting blades 18b shown in FIGS. 7 and 8, cutting blades 18a' and 18b' have first or rearward, and second or side, cutting edges 60' and 62', respectively. First or rearward cutting edge 60' extends generally along the trailing edge 70' of blades 18a' and 18b' and second or side cutting edge 62' depends inwardly from one side 72' of blades 18a' and 18b', generally transverse to first cutting edge 60'. However, whereas both of the outer and inner faces 80 and 64 of cutting blades 18a and 18b are substantially planar and have substantially rectangular configurations, only the inner face 64l of cutting blades 18a' and 18b' is substantially planar. The outer face 80' of cutting blades 18a' and 18b' has a complex convex surface, as shown in FIGS. 14-18. By a complex convex surface is meant a surface which is convex in both the axial and transverse directions. Outer face 80' has a complex convex surface because this is the surface which meets the vein wall; a complex convex surface is smooth and will not damage the vein wall.

Sides 72' and 78' of cutting blades 18a' and 18b' are substantially parallel forwardly of first cutting edge 60', but taper inwardly at first cutting edge 60'. First cutting surfaces 60a' and 60b' being concave in the transverse direction, as shown in FIGS. 16a and 16b.

As shown in FIGS. 16-18, cutting blades 18a' and 18b' are attached to flat spring wire elements 24' and 26' offset from the longitudinal center lines of cutting blades 18a' and 18b', being positioned between the longitudinal center line C (FIGS. 17 and 18) and the side 78'. Thus, when cutting blades 18a' and 18b' are fully retracted, wire elements 24' and 26' will lie side-by-side.

Cutting blades 18a' and 18b' are respectively affixed to wire elements 24' and 26' in the same manner as cutting blades 18a and 18b are respectively affixed to wire elements 24 and 26. Wire elements 24' and 26' also preferably comprise flat wire springs, as flat wires take up less space in hollow tubular member 12 than wires having a circular cross-section. However, wires having a circular cross-section can also be used.

End member 38' of valvulotome 10' also has a different shape than end member 38 of valvulotome 10. In order to better accommodate the configuration of cutting blades 18a' and 18b' end member 38' is frusto-conical, having sides which taper inwardly towards the base. Thus, even if cutting blades 18a' and 18b' for some reason do not seat properly within end member 38' when they are retracted, their cutting edges 60' will bear against the exterior of end member 38' and thereby be protected from contact with the surrounding tissue. End member 38' can have provided therein a coil spring 56 as described above with respect to end member 52 shown in FIG. 5.

As a result of the configuration of cutting blades 18a' and 18b', the second cutting edges 62' and the parallel portions of sides 72' and 78' matingly register or engage when cutting blades 18a' and 18b' are in the retracted position, as shown in FIGS. 15 and 18, and first cutting edges 60' are seated in end member 38, as shown in FIG. 15. In this way, the cutting edges of cutting blades 18a' and 18b' are guarded against contact with the surrounding tissue when cutting blades 18a' and 18b' are retracted.

Referring now to FIGS. 23-30, there is shown a third embodiment of the adjustable intraluminal valvulotome 10" according to the invention. As shown in FIGS. 23 and 24, valvulotome 10" includes a hollow tubular member 12, a wire member 14, and a handle 16 essentially identical to hollow tubular member 12, wire member 14, and handle 16, respectively described above with respect to valvulotome 10 shown in FIGS. 1-8. Cutting blades 18a" and 18b" are mounted to spring wire elements 24" and 26", respectively, and wire elements 24" and 26" are attached to wire member 14 at a joint 30 as shown in FIG. 3 with respect to valvulotome 10. Valvulotome 10" differs from valvulotomes 10 and 10' primarily, but not exclusively, in the configuration of its cutting blades 18a" and 18b".

As can be seen from FIGS. 23 and 24, cutting blades 18a" and 18b" are identical. Referring to FIGS. 25-29, cutting blade 18a" is shown, it being understood that as cutting blades 18a" and 18b" are identical, they will both be described with respect to FIGS. 25-29.

Like cutting blades 18b shown in FIGS. 7 and 8, and cutting blades 18b' shown in FIGS. 16 and 17, cutting blades 18a" and 18b" have first or rearward, and second or side, cutting edges. First or rearward cutting edge 60" extends generally along the trailing edge 70" of blades 18a" and 18b" and second or side cutting edge 62" depends inwardly from one side 72" of blades 18a" and 18b', generally transverse to first cutting edge 60". Also, like outer face 80' of cutting blades 18a' and 18b', outer face 80" of cutting blades 18a" and 18b" has a complex convex surface, as shown in FIGS. 25-29. However, inner face 64" of cutting blades 18a" and 18b" has a complex concave surface, as also shown in FIGS. 25-29. By a complex concave surface is meant a surface which is concave in both the axial and transverse directions.

Also, as best shown in FIG. 26, the outer face 80" has a substantially trapezoidal configuration with rounded leading and trailing edges 74" and 70", when seen in plan view. In addition, sides 72" and 78" are formed with upper linear portions 72a" (FIG. 27) and 78a" (FIG. 25), respectively, configured to register or engage with each other when cutting blades 18a" and 18b" are in the fully retracted position, as shown in FIG. 24. First and second cutting edges 60" and 62" can be formed by grinding trailing edge 70" and side 72" at an angle. The other side 78" and leading edge 74" of cutting blades 18a" and 18b" are smooth.

Like cutting blades 18a' and 18b', cutting blades 18a" and 18b" are attached to flat spring wire elements 24" and 26" offset from the longitudinal center lines of cutting blades 18a" and 18b", being positioned between the longitudinal center lines and the sides 72" and 80". Cutting blades 18a" and 18b" are respectively affixed to wire elements 24" and 26"" in the same manner as cutting blades 18a and 18b, respectively, and 18' and 18b', respectively, are affixed to wire elements 24 and 26. Wire elements 24" and 26" also preferably comprise flat wire springs. However, as best shown in FIGS. 25 and 27, wire elements 24" and 26" differ from wire elements 24 and 26 in that wire elements 24" and 26" are bent at an obtuse angle at a point 90 generally opposite cutting edge 60". This bend ensures that cutting blades 18a" and 18b" come together properly when they are retracted.

End member 38" of valvulotome 10" also has a different shape than end members 38 and 38' of valvulotomes 10 and 10'. In order to better accommodate the configuration of cutting blades 18a" and 18b", end member 38" is cup-shaped, having rounded sides which taper inwardly towards the base. Thus, even if cutting blades 18a" and 18b" for some reason do not seat properly within end member 38 when they are retracted, their cutting edges 60" will bear against the exterior of end member 38" and thereby be protected from contact with the surrounding tissue. End member 38" can have provided therein a coil spring 56 as described above with respect to end member 52 shown in FIG. 5.

As a result of their configuration, the leading edges 74" of cutting blades 18a" and 18b" meet, so that opposed linear portions 72a" and 78a" register with each other and first cutting edges 60" are seated in end member 38", when cutting blades 18a" and 18b" are in the fully retracted position, as shown in FIG. 24. In this way, the cutting edges of cutting blades 18a" and 18b" are guarded against contact with the surrounding tissue when cutting blades 18a" and 18b" are retracted.

Figure 9:
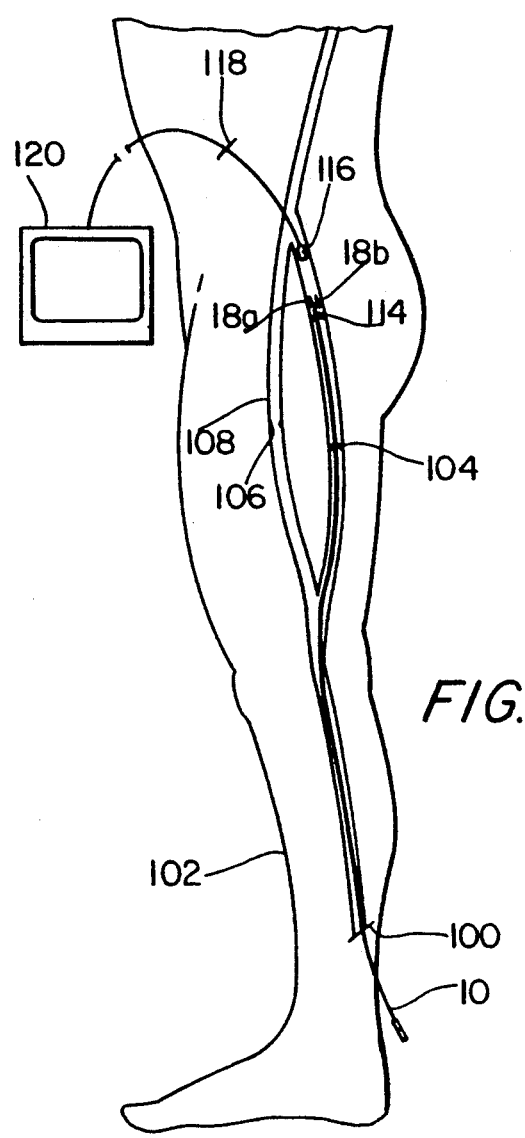
FIG. 9 is a schematic representation of a leg with a blocked femoral artery which has been bypassed with a vein in which has been inserted a valvulotome and angioscope.

The method of using the intraluminal valvulotomes 10, 10' and 10" according to the invention is shown in FIGS. 9-12, 19-22, and 30. As shown in FIG. 9, an incision 100 is made in leg 102 proximate vein 104 that has been used to bypass blockage 106 in artery 108. The adjustable intraluminal valvulotome 10, 10', or 10" is inserted through the incision and advanced into vein 104 to a distance that places end member 38 adjacent to but not beyond valve 114 which is to be rendered inoperative. If a number of valves are to be ruptured, the valvulotome 10, 10', or 10" is inserted up to the farthest valve and then the valves can be ruptured in sequence starting with the farthest valve first and ending with the valve nearest the incision Angioscope 116 (FIG. 10) can be inserted through incision 118 and be used to monitor the position of cutting blades 18a and 18b, 18a' and 18b', or 18a" and 18b" on monitor 120.

Figure 10:
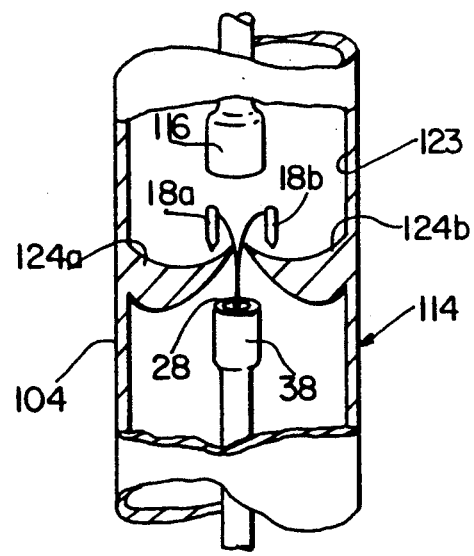
FIG. 10 is a lateral cross sectional view of a vein with venous valve in which has been inserted the valvulotome according to FIG. 1 along with an angioscope.
Figure 12:
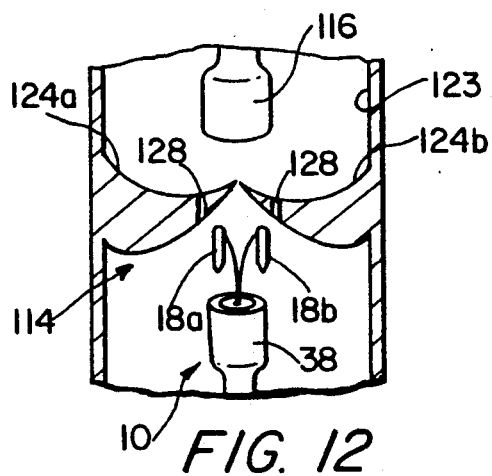
FIG. 12 is a cross-sectional view of the vein and venous valve of FIG. 10, showing retraction of the cutting blades after engaging with and rupturing the valve cusps.
Figure 13:
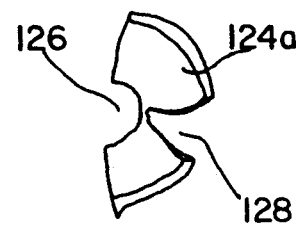
FIG. 13 is a detailed view of a single ruptured valve cusp.
Figure 19:
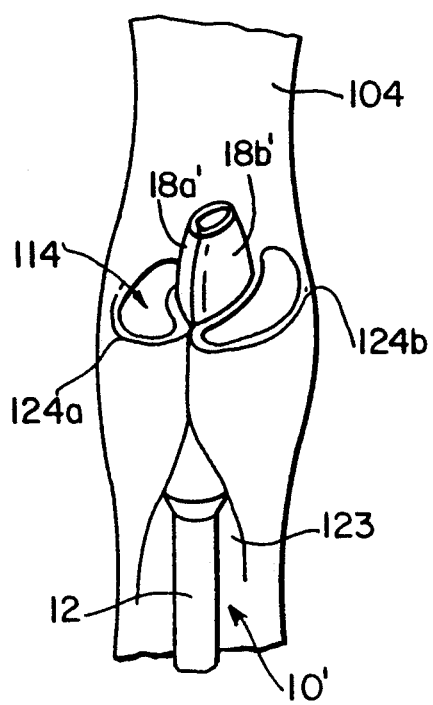
FIG. 19 is a perspective view of a vein and venous valve showing insertion of the cutting blades in the retracted position between the valve cusps.
Figure 20:
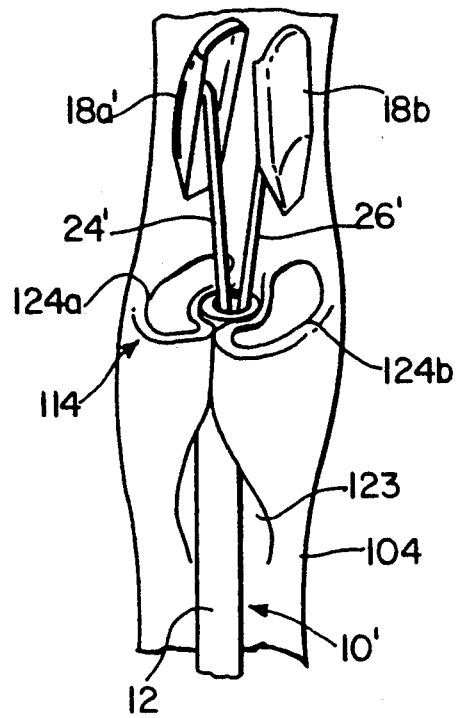
FIG. 20 is a perspective view of a vein and venous valve showing extension of the cutting blades prior to rupturing the valve cusps.
Figure 21:
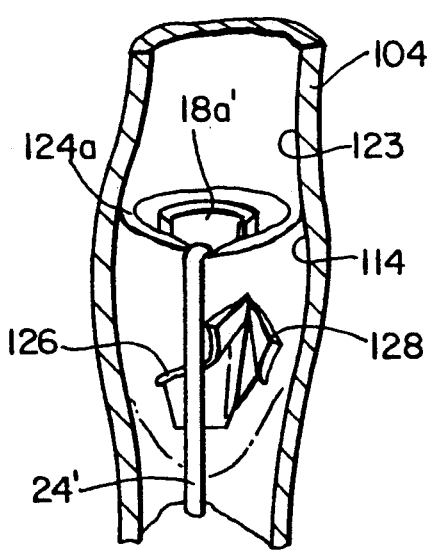
FIG. 21 is a perspective view of a vein and venous valve showing the cutting blades in the process of rupturing the valve cusps.
Figure 22:
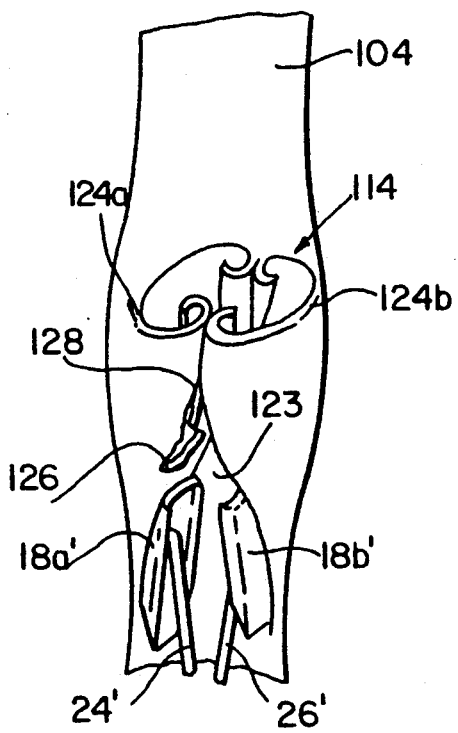
FIG. 22 is a perspective view of a vein and venous valve showing the cutting blades withdrawn from the venous valve following rupture of the valve cusps.

Once valvulotome end member 38, 38', or 38" has been advanced proximate valve cusps 124a, 124b of valve 114, as shown in FIG. 19, cutting blades 18a and 18b, 18a' and 18b', or 18a" and 18b" are extended longitudinally and radially outward beyond valve cusps 124a, 124b as shown in FIGS. 10 and 20, until interblade spacing shown by arrow 121b is sufficient to engage with the valve cusps 124a, 124b, but not too wide so as to damage inner wall 123. Angioscope 116 can be used to monitor the positioning and extension of the blades as shown in FIG. 11. Cutting blades 18a and 18b, 18a' and 18b', or 18a" and 18b" are then retracted as shown FIGS. 21 and 30, causing the blades to engage with and cut valve cusps 124a, 124b along lines 126, 128 as shown in FIGS. 11, 12, and 22, rupturing the valve cusps and rendering valve 114 inoperative. Cutting blades 18a and 18b, 18a' and 18b', or 18a" and 18b" can then be fully retracted into a completely shielded position. Valvulotome end member 38, 38', or 38" can then e repositioned proximate the next valve to be rendered inoperative. The surgeon repeats the steps of extending the cutting blades beyond the valve cusps and retracting the blades, causing them to engage with, cut and rupture the subsequent valve cusps. This procedure is repeated for each of the valves that are to be rendered inoperative. As an aid to the surgeon, angioscope 116 can be utilized to ensure that all the valves have been properly ruptured. Most importantly, if the surgery needs to be aborted, the valvulotome with cutting blades 18a and 18b, 18a' and 18b', or 18a" and 18b", in their fully retracted and shielded position, may be withdrawn from the vein without any damage to the valve cusps or the inner walls of the vein.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. An adjustable intraluminal valvulotome comprising:
    a hollow tubular member having a distal end and a proximal end;
    first and second substantially identical, opposed cutting blades movable between an extended position and a retracted position with respect to said distal end of said tubular member and between an open position in which said cutting blades are spaced apart from each other and a closed position in which said cutting blades are drawn tightly against each other, said cutting blades being in said closed position when in said retracted position and in said open position when in said extended position, each of said cutting blades having a complex concave inner surface, a complex convex outer surface, a forward blunt edge in the direction of extension, a rearward cutting edge in the direction of retraction, and a pair of opposed side edges, one of said side edges being a blunt edge and the other of said side edges being a cutting edge, said inner surfaces of said cutting blades substantially facing each other in all said positions and said forward blunt edges meeting when said cutting blades are in said closed and retracted positions;
    control means slidably disposed within said hollow tubular member for moving said first and second cutting blades between said extended and retracted positions and a plurality of partially-extended positions intermediate said extended and retracted positions;
    spacing means for moving said first and second cutting blades laterally apart from each other from said closed position to said open position as said control means moves said cutting blades from said retracted position to said extended position; and
    shielding means for shielding at least said rearward cutting edges of said first and second cutting blades in said retracted and closed positions.

2. The valvulotome of claim 1, wherein said side cutting edges extend inwardly from said inner surfaces of said cutting blades, whereby said side cutting edges are shielded from contact with any surrounding tissue when said cutting blades are in said closed position.

3. The valvulotome of claim 1, wherein said spacing means comprises biasing means for biasing said first and second cutting blades laterally apart from each other.

4. The valvulotome of claim 1, wherein said control means comprises a first wire element having proximal and distal ends, said distal end thereof being attached to said first cutting blade, and a second wire element having proximal and distal ends, said distal end thereof being attached to said second cutting blade.

5. The valvulotome of claim 4, wherein said control means further comprises a third wire element connected to said proximal ends of said first and second wire elements.

6. The valvulotome of claim 4, wherein said first and second wire elements each have a bend therein in the vicinity of said rearward cutting edges 7. The valvulotome of claim 1, wherein said shielding means comprises receptacle means formed at said distal end of said tubular member for enclosing at least a portion of said first and second cutting blades.

8. The valvulotome of claim 7, wherein said receptacle is cup-shaped and has sides which taper inwardly in the direction of retraction.

* * * * *